(12) United States Patent
Martinez

(10) Patent No.: US 7,463,917 B2
(45) Date of Patent: Dec. 9, 2008

(54) ELECTRODES FOR SUSTAINED DELIVERY OF ENERGY

(75) Inventor: Gonzalo Martinez, Mendota Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 177 days.

(21) Appl. No.: 10/862,214

(22) Filed: Jun. 7, 2004

(65) Prior Publication Data

US 2005/0246002 A1 Nov. 3, 2005

(51) Int. Cl.
*A61N 1/04* (2006.01)
(52) U.S. Cl. ............ 600/395; 607/119; 607/121; 600/372
(58) Field of Classification Search .......... 607/121; 600/372, 395
See application file for complete search history.

(56) References Cited

U.S. PATENT DOCUMENTS

| | | | |
|---|---|---|---|
| 4,969,468 A | 11/1990 | Byers et al. | |
| 5,571,158 A * | 11/1996 | Bolz et al. | 607/121 |
| 5,683,443 A | 11/1997 | Munshi et al. | |
| 5,957,958 A | 9/1999 | Schulman et al. | |
| 6,135,990 A | 10/2000 | Heller et al. | |
| 6,189,536 B1 * | 2/2001 | Martinez et al. | 128/897 |
| 6,240,320 B1 * | 5/2001 | Spehr et al. | 607/122 |
| 6,267,866 B1 * | 7/2001 | Glesener et al. | 205/450 |
| 6,592,519 B1 | 7/2003 | Martinez | |
| 2002/0111601 A1 * | 8/2002 | Thompson | 604/514 |
| 2003/0036691 A1 * | 2/2003 | Stanaland et al. | 600/372 |
| 2003/0199741 A1 * | 10/2003 | Martinez | 600/309 |
| 2006/0003310 A1 * | 1/2006 | Klauke et al. | 435/4 |

OTHER PUBLICATIONS

Xu, J. et al.; Boron-Doped Diamond Thin-Film Electrodes:; Analytical Chemistry, American Chemical Society.; vol. 69, No. 19, Oct. 1997, pp. 591A - 597A.

Durst, R.A. et al.; "Chemically Modified Electrode: Recommended Terminology and Definitions"; Pure and Applied Chemistry, vol. 69, No. 6, 1997, pp. 1317-1323.

* cited by examiner

*Primary Examiner*—Carl H Layno
*Assistant Examiner*—Yun Haeng Lee
(74) *Attorney, Agent, or Firm*—Daniel G. Chapik

(57) ABSTRACT

Electrodes include a coating that provides a barrier to fluids and ions within a biological environment. The coating increases the overpotential of the electrode. The coating permits the introduction and use of the electrodes into biological environments without the detrimental complications of electro-chemical reactions typically present with the use of metal and metal-alloy electrodes in such environments.

37 Claims, 9 Drawing Sheets

ELECTRODES FOR SUSTAINED DELIVERY OF ENERGY

FIELD OF THE INVENTION

The invention relates to medical devices and, more particularly, to electrodes for medical devices.

BACKGROUND

Electric fields may be beneficial in providing therapies related to a number of medical conditions. Many known therapies utilize application of electric fields to patients. These electric fields may be AC or DC fields that are applied locally to a small, precise location of a patient's body, or to larger regions that may include entire organs.

Implantable medical devices, such as cardiac pacemakers or cardioverter-defibrillators, include leads that deliver therapeutic electrical stimulation to the heart in the form of pacing, cardioversion or defibrillation pulses. The pulses are delivered to the heart via electrodes disposed on the leads, typically near distal ends of the leads. The leads serve to position the electrodes with respect to various cardiac locations to deliver electrical stimulation pulses to appropriate locations. Leads are also used for sensing purposes, or both sensing and stimulation purposes.

In addition, implantable leads are used in neurostimulation devices for deep-brain stimulation, spinal cord stimulation, sacral stimulation, and gastrointestinal tract stimulation. Leads are also used with a wide variety of other medical devices including, for example, devices that provide muscular stimulation therapy, devices that sense chemical conditions in a patient's blood, gastric system stimulators, implantable lower colon stimulators, e.g., in graciloplasty applications, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and the like. In summary, medical leads can be used for sensing purposes, stimulation purposes, drug delivery, and so forth. These exemplary uses of implantable leads typically involve energizing the leads for relatively short periods of time.

Implanted electrodes function in a harsh biological environment and are often exposed to a variety of fluids. Over time, sustained electric fields may cause electro-chemical reactions to occur at the electrodes, resulting in corrosion. Corrosion can be particularly problematic in environments that contain biological fluids, such as water. Electrode corrosion has generally limited the use of electric fields for therapy to short, durational, or intermittent electrical fields.

SUMMARY

In general, the invention is directed to an electrode for delivering a sustained supply of electrical energy to support the generation of an electric field for therapy. The electrode includes a coating layer to provide a barrier between the electrode and a surrounding fluid environment. The coating layer eliminates or reduces the effects of unwanted electro-chemical reactions that typically arise from the sustained presence of electric fields in fluids, including water.

The coating layer increases the overpotential of interest for the electrode and permits larger electric fields to be applied on a sustained basis while reducing adverse effects, such as electrode corrosion, typically caused by electro-chemical reactions. The overpotential refers to a difference in electric potential between an open circuit, equilibrium potential of an electrode material in a fluid environment, and an applied electric potential at which an undesired chemical reaction, such as water breakdown, occurs. As used herein, overpotential means the overpotential of interest, which is based upon the material under consideration. For example, for water, the overpotential of interest is the overpotential at which water breakdown occurs. Thus, this magnitude will depend upon the material being considered. Any relevant fluid or gas may be the material of interest.

In one embodiment, the invention provides an electrode comprising an electrically conductive substrate layer, an electrical conductor coupled to the conductive substrate layer, and a coating layer surrounding at least a portion of the substrate layer, wherein the coating layer provides an increased overpotential for the electrode in a fluid.

In another embodiment, the invention provides a medical device comprising a first electrode, a second electrode and an electric power source. The first electrode has a first electrically conductive substrate layer, a first electrical conductor coupled to the first substrate layer, and a first coating layer surrounding at least a portion of the first substrate layer. The first coating layer provides an increased overpotential for the first electrode in a fluid. The second electrode has a second electrically conductive substrate layer, a second electrical conductor coupled to the conductive substrate layer, and a second coating layer surrounding at least a portion of the second substrate layer. The second coating layer provides an increased overpotential for the second electrode in a fluid. The electrical power source is coupled to apply a substantially continuous electric potential across the first and second electrical conductors.

In an added embodiment, the invention provides a method comprising implanting an electrode array within a patient, implanting an implantable component within a patient, energizing the electrode array to create a sustained electric field that interacts with the implantable component, and controlling the electric field to modify the implantable component to deliver therapy.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

Figure 1:
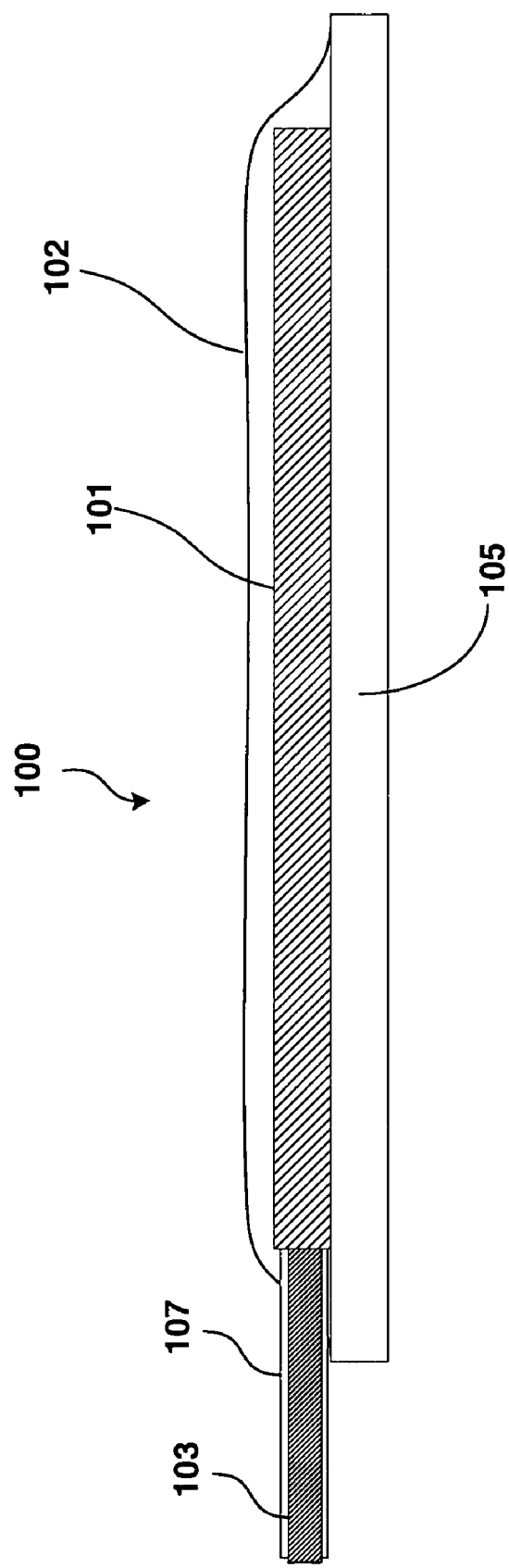
FIG. 1 is a cross-sectional side view illustrating an example of an electrode for providing sustained electric fields according to an embodiment of the invention.

FIG. 1 is a schematic diagram illustrating an example of an electrode for providing sustained electric fields according to an embodiment of the invention. The term "sustained," as used herein, generally refers to an electric field or therapy delivered on a substantially continuous basis over period of time, e.g., several seconds, minutes, or hours, in contrast to electrical pulses applied on an extremely short, intermittent basis, e.g., in therapeutic intervals of substantially less than about one second. This delineation refers to the delivery of therapy and not to the frequency or pulse duration of the generated signal. That is, therapy is delivered continuously for one or more seconds, but during that time frame multiple pulses, bursts, or oscillations of any frequency may be delivered. Of course, a single continuous pulse having a long pulse width could also be utilized, but is not required to provide sustained delivery, as used herein. Electrode 100 is one of a pair of electrodes, forming a cathode and anode, used to generate a sustained electric field for use in providing therapies to a patient. Electrode 100 includes an electrically conductive monolithic substrate layer 101, a coating layer 102, and an optional backing layer 105. For operation, electrically conductive substrate layer 101 is electrically coupled to an electric power source (not shown in FIG. 1) via an electrical conductor 103. Conductor 103 is covered by an insulating layer 107. In some embodiments, electrical conductor 103 may be an implantable lead, e.g., for generation of electric fields internally within a patient. Alternatively, electrical conductor 103 may be a simple electrical cable for external applications.

Substrate layer 101 is covered by coating layer 102, which provides a physical barrier between substrate layer 101 and the surrounding environment. Coating layer 102 provides a protective layer that reduces degradation of conductive substrate layer 101 during prolonged use in fluid environments, but does not significantly undermine electrical performance of electrode 100 in therapy applications. As will be described, coating layer 102 is formed from a material selected to increase the overpotential of electrode 100. The increased overpotential permits larger electric fields to be applied on a sustained basis with reduced adverse effects, such as electrode corrosion, that would otherwise be caused by electro-chemical reactions.

In the example of FIG. 1, electrode 100 also includes backing layer 105 upon which substrate layer 101 and coating layer 102 are formed. Backing layer 105 provides physical support and structural integrity to electrode 100 and facilitates placement or implantation of the electrode within or on a patient. However, backing layer 105 is optional. In other embodiments, substrate layer 101 may sufficiently support the structure of electrode 100 without the use of backing layer 105.

In operation, a pair of appropriately positioned electrodes 100 serves as an anode and cathode, respectively, to generate an electric field. The electric field is created to pass through at least a portion of a patient's body situated between the electrodes 100 to provide any of a variety of desired therapies. Both electrodes 100 may be placed internally within patient or externally, depending on the desired therapy. In some embodiments, one electrode 100 may be placed internally with the other electrode placed externally.

An electrical power source (not shown in FIG. 1) is coupled to apply an electric potential across the pair of electrodes, thereby creating the electric field, on a sustained basis. In some embodiments, the electrical power source generates a time-varying signal, which is coupled across the pair of electrodes 100 to generate a time-varying electric field. The time-varying electric field may consist of either mono-phasic pulses or bi-phasic pulses, depending upon the particular therapy selected.

In other embodiments, the electrical power source delivers a non-varying signal. In each case, the electrical potential applied by the electrical power source is delivered substantially continuously, such that the electric potential and resulting electric field are not interrupted by significant periods during which the varying or non-varying potential is not supplied. In other words, generation of the electric field on a sustained basis is achieved by application of a substantially continuous electric potential waveform, in contrast to application of short, intermittent pulses or pulse trains.

Sustained electric fields generated within biological fluids, especially water, result in electro-chemical reactions at the exposed surface of the electrodes. Typically, these electro-chemical reactions result in a measured potential drop across the interface between the surface of the working electrode and the biological fluid (i.e., an interfacial potential). However, it is difficult to control or measure this interfacial potential without placing another electrode in the biological fluid. Thus, a reference electrode is typically used to measure the interfacial potential. One widely used and well-known reference electrode for measuring an interfacial potential is a saturated calomel electrode. Electro-chemical reactions also may occur on external electrodes as electric fields promote reaction of hydrogels present between a patient's skin and the electrode's surface. The characteristics of these reactions are typically related to the magnitude of the electrical potential generated at the electrodes, as well as the length of time the electrical potential is applied.

The overpotential refers to a difference in electric potential between an open circuit, equilibrium potential of an electrode material in a fluid environment, and an applied electric potential at which an undesired chemical reaction, such as water breakdown, occurs. As used herein, overpotential means the overpotential of interest, which is based upon the material under consideration. For example, for water, the overpotential of interest is the overpotential at which water breakdown occurs. Thus, this magnitude will depend upon the material being considered and the effect produced, such as fluidic breakdown into gaseous components or other chemical or material transitions. Any relevant fluid or gas may be the material of interest.

Overpotential ($\square$) is the electrical potential (voltage), that must be applied in an electrolytic cell over the open-circuit (equilibrium) potential to cause a chemical reaction with a given substance in contact with the surface of an electrode. When an electrode is used in the presence of biological fluids, such as water, the overpotential corresponds to the voltage at the electrode where water is separated in to hydrogen and oxygen components. The value for this overpotential depends on the electrode material and the current density. Typically, overpotential values are measured relative to an open circuit, equilibrium potential, which may be obtained from a reference electrode, such as the saturated calomel electrode mentioned above. A coating layer, as described herein, increases the overpotential of the electrode and permits larger electric fields to be applied on a sustained basis while reducing adverse effects, such as electrode corrosion, typically caused by electro-chemical reactions.

The separation of water into hydrogen and oxygen can result in corrosion of electrodes, due to large pH changes. This corrosion of electrodes within biological environments is undesirable, because the electrodes may be rendered inoperable or less effective. When substantial corrosion occurs, implanted electrodes must be explanted and replaced, subjecting the patient to the pain and inconvenience of an additional surgical procedure. In accordance with the invention, electrodes constructed from materials having a higher overpotential may be used to generate electric fields using larger voltages on a sustained basis without the generation of electro-chemical reactions sufficient to cause substantial corrosion. For example, providing a coating layer 102 on electrode 100, in accordance with the invention, increases the overpotential of electrode to reduce corrosion. In this manner coating 102 permits electrode 100 to support the application of larger voltages and sustained electric fields over an extended period of time.

Figure 2:
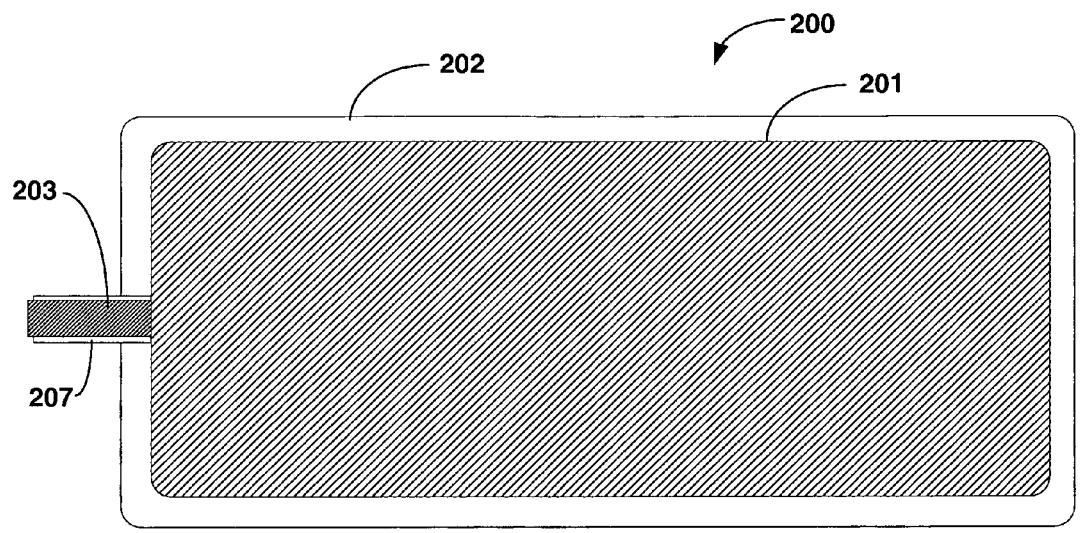
FIG. 2 is a plan view illustrating another example of an electrode for providing sustained electric fields according to an embodiment of the invention.
Figure 3:
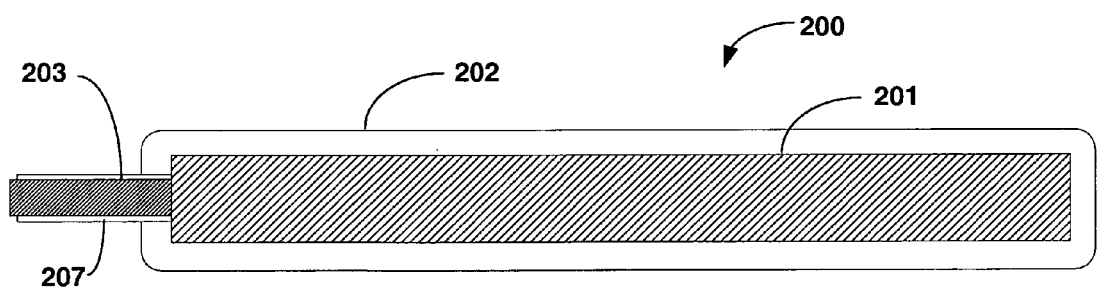
FIG. 3 is a cross sectional side view of the electrode of FIG. 2.

FIG. 2 is a plan view illustrating an embodiment of an electrode 200. FIG. 3 is a cross-sectional side view of electrode 200 of FIG. 2. The electrode 200 of FIGS. 2 and 3 substantially conforms to the structure of electrode 100 of FIG. 1, and comprises a substrate layer 201 and a coating layer 202. However, electrode 200 does not incorporate the optional backing layer. Instead, substrate layer 201 is selected to have a thickness or rigidity sufficient to provide structural integrity to electrode 200. As shown in FIG. 2, coating layer 202 substantially encapsulates substrate layer 201, providing a barrier between the substrate layer and an environment in which electrode 200 is deployed. Substrate layer 201 comprises an electrically conductive material. As examples, the electrically conductive material may be any of a variety of metals, alloys, conductive silicons, semiconductor material, and similar conductive materials, alone or in various combinations, which are fabricated into a desired size and shape. Non-limiting examples of metal materials for fabrication of electrically conductive substrate layer 201 include platinum iridium alloys, titanium nitride, platinized platinum (platinum oxide), platinum coated with iridium oxide, titanium coated with iridium oxide. Other examples include silver, silver chloride, tin and tin alloys, gold, stainless steel, refractory metals such as niobium, tantalum, zirconium alloys, cobalt, nickel alloys, and ferromagnetic alloys.

Coating layer 202 is formed from a dielectric or semiconducting material that provides a high overpotential value for electrode 200. In some embodiments, the material used to form coating layer 202 may be generally inert, and provide a barrier to water, chloride and other reactive ions. In one embodiment, for example, the material forming coating layer 202 is a boron-doped diamond material. As an example, the boron-doped diamond material may be a carbon-based diamond material in which boron ions have been added at a concentration in a range of approximately 2000 to 10000 parts per million. Such a material tends to produce a very high oxygen overpotential.

The coating material used for coating layer 202 may include, either alone or in combination, other suitable materials such as diamond-like carbon (DLC), borosilicate glass, tantalum pentoxide, titanium nitrides, silicon nitrides, titanium oxides, and other carbides, nitrides, dielectrics and doped dielectrics, as well as organic and inorganic nanostructures or films. The coating layer 202 provides a physical barrier between, e.g., the water molecules within biological fluids, and substrate layer 201 of electrode 200. Again, the coating layer 202 increases the overpotential of electrode 200. An increased overpotential of at least approximately 1.2 volts permits a given electrode 200 to apply an increased electric field for a sustained period of time without significant damage due to undesired electro-chemical reactions. In certain embodiments, the increased overpotential is at least approximately 1.8 volts. As such, electrodes with coating layer 202 exhibit higher overpotentials, and therefore may be used in providing therapies utilizing sustained electric fields.

As further shown in FIGS. 2 and 3, electrode 200 includes an electrical conductor 203, with an insulating layer 207, that provides a connection to other circuit elements such as an electrical power generator (not shown in FIG. 2A). Although illustrated as rectangular in shape, electrode 200 may be constructed in a wide variety of configurations, shapes or sizes. For example, depending on the application, electrode 200 may be a plate-like electrode in a circular, oval-like, or rectangular shape. Alternatively, electrode 200 may be formed as a ring-electrode, e.g., for deployment on a medical lead. In addition, electrode 200 may include or be coupled to an active or passive fixation mechanism, such as tines, barbs, or a helical coil for internal applications, or conductive adhesives for external applications.

Coating layer 202 is, in one embodiment, a thin film fabricated using well known thin film deposition techniques such as sputtering, vapor deposition, ion beam deposition, or other deposition methods. Photolithography or other etching techniques may be applied to pattern coating layer 202 in a desired pattern relative to the underlying substrate layer 201 and electrical conductor 203. Coating layer 202 is constructed to be extremely thin to avoid the creation of undesired resistive effect between substrate layer 201 and coating layer 202 while remaining thick enough to provide a complete barrier overpotential. for electrode 200, and thereby reduce damage otherwise caused by electro-chemical reactions. In certain embodiments, coating layer 202 has a thickness of about 1-10,000 nm.

In some embodiments, the coating layer 202 is thinner than about 1 nm and has a dielectric constant of about 4 or higher. However, depending upon the material chosen and the application techniques, coatings thinner than 1 nm might not be sufficiently continuous to provide the desired characteristics of a higher overpotential. Thus, coating layer 202 having a thickness of between about 1-3 nm provides a balance between higher overpotentials and acceptable levels of capacitance. As such, coating layer 202 with a thickness less than about 3 nm but greater than about 1 nm may provide a good balance between capacitance and overpotential.

In other embodiments, coating layer 202 may be as thick as about 100 nm and still produce an appropriate balance between capacitance and overpotential. Greater thicknesses may permit the use of alternative coating processes such as dip coating, spin coating, spray coating, or the like. The use of thicker coatings, however, may result in the creation of resistive effects that may not be desired depending upon the application. One skilled in the art will recognize that the thickness of the coating may be varied consistent with the teachings of this disclosure.

Figure 4:
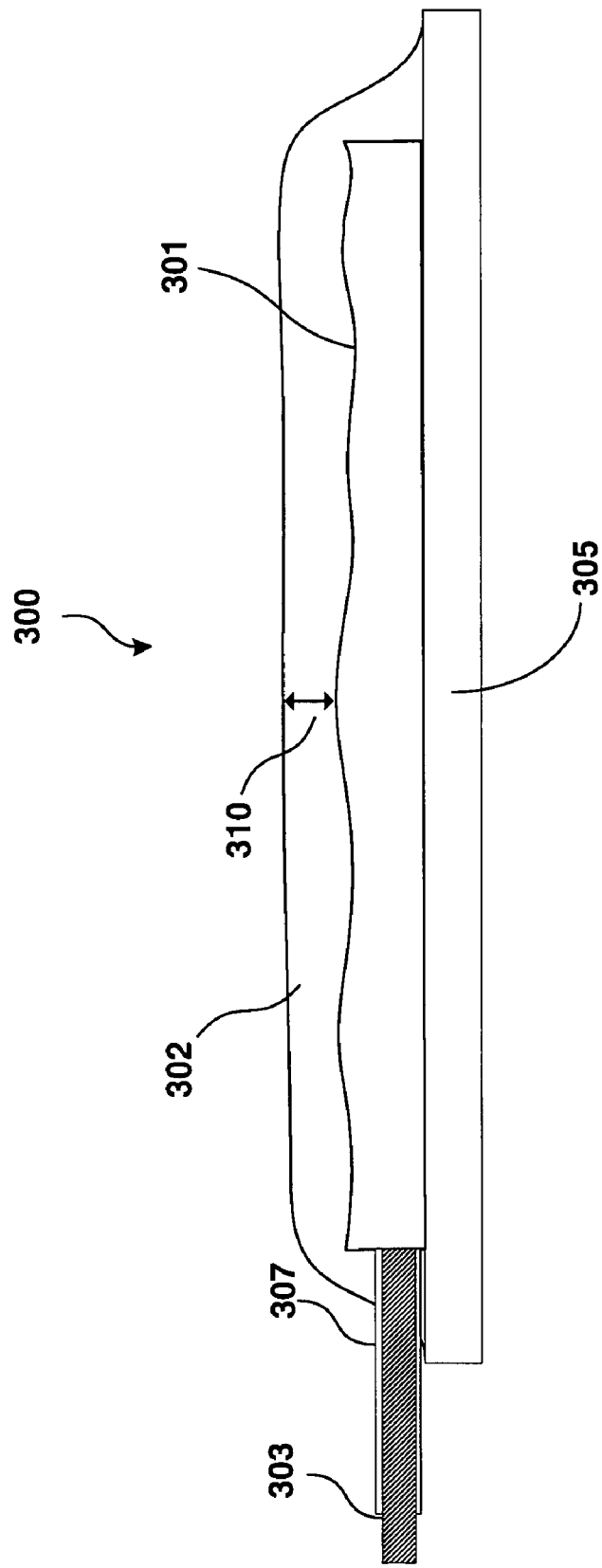
FIG. 4 is a cross sectional side view of an electrode illustrating surface roughness of an electrically conductive substrate layer relative to a coating layer.

FIG. 4 is a cross sectional side view of an electrode 300 illustrating surface roughness of an electrically conductive substrate layer 301 relative to a coating layer 302. As shown in FIG. 4, electrode 300 further includes an electrical conductor 303 and an insulating layer 307. In order to fabricate the electrode 300 with a coating layer 302 that provides a physical barrier between the biological environment in which electrode 300 is used, coating layer 302 should be thick enough to cover the substrate 301, including any surface irregularities in the surface of substrate 301. Thus, the surface roughness of substrate 301 will define a minimum coating thickness. Substrate layer 301 may be polished to achieve the desired surface roughness using any well known polishing techniques such as ion milling, centerless grinding, electro-polishing and other similar polishing techniques known in the art, prior to the application of the coating material so as to permit a thinner, continuous coating.

The surface roughness of substrate layer 301 contributes to both resistive and capacitive properties of coating layer 302. The resistive properties of coating layer 302 are defined as:

$$R = \rho \frac{d}{A} \quad (1)$$

where d corresponds to the thickness 310 of coating layer 302,

A corresponds to the surface area of substrate layer 301, and

ρ corresponds to the resistivity of the material used to form substrate layer 301.

The capacitive properties of coating layer 302 are defined as:

$$C = \frac{\varepsilon o k A}{d} \quad (2)$$

where d corresponds to the thickness 310 of coating layer 302,

A corresponds to the surface area of substrate layer 301, and $\epsilon o * k$ represents relative permittivity.

Thus, the thickness 310 of coating layer 302 will affect both the resistive and capacitive properties of the completed electrode 300, in an inverse manner. Furthermore, since the required thickness is related to the surface roughness of the substrate 301, selecting, controlling or modifying that surface roughness permits different thicknesses 310 to be achieved. In one embodiment, the surface roughness of substrate layer 301 is less than 10% of the thickness 310 of coating layer 302. For example, substrate layer 301 may be polished to this desired roughness, i.e., degree of smoothness, prior to fabrication of coating layer 302.

Figure 5:
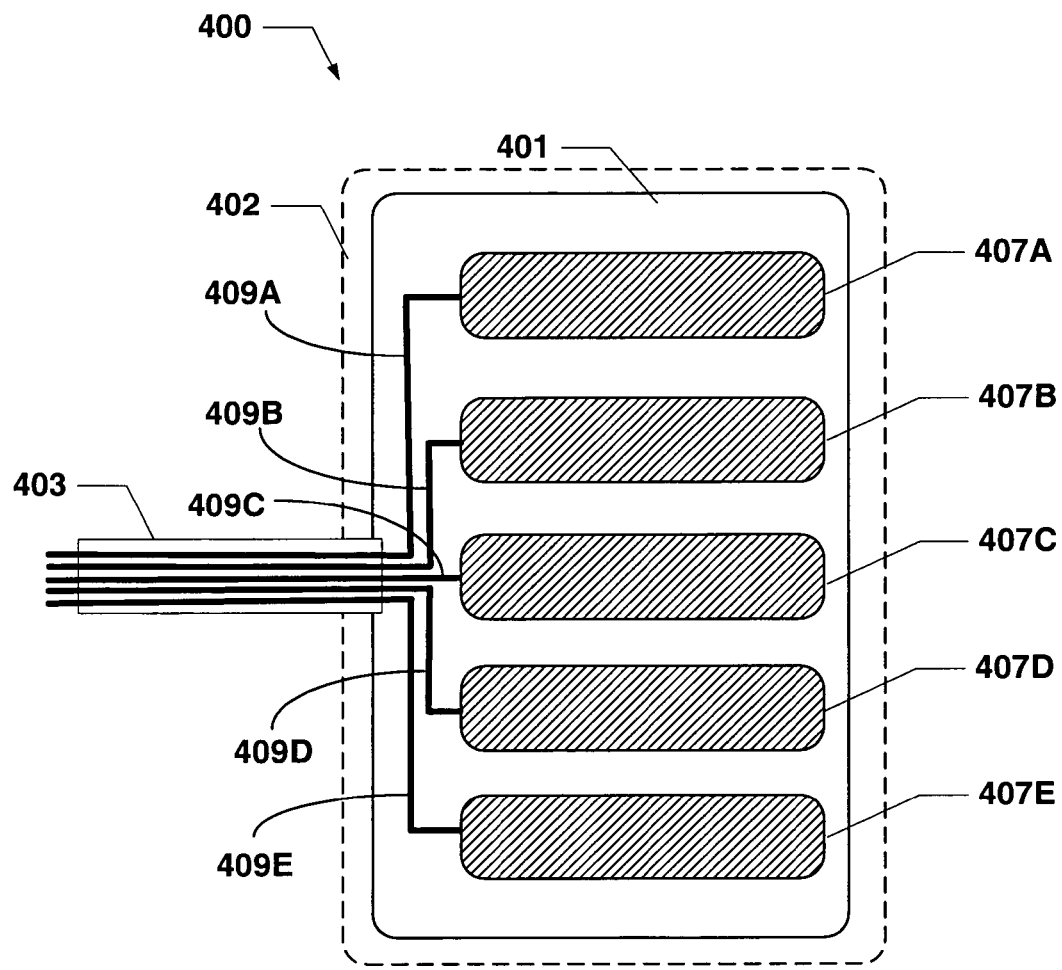
FIG. 5 is a schematic diagram of a multi-element electrode array used to generate a sustained electric field according to an embodiment of the invention.

FIG. 5 is a schematic diagram of a multi-element electrode array 400. In this embodiment, the electrode array 400 includes a backing layer 401, a coating layer 402 and one or more electrical conductors in a common electrical cable or lead 403. As shown in FIG. 5, a plurality of electrodes 407A-407E (collectively referred to as "electrode array elements 407") are formed on backing layer 401. Each of the electrode array elements 407 is a separate, individually controlled, electrically conductive substrate element.

In one embodiment, each of the electrode array elements 407 is electrically coupled to a separate electrical conductor 409A-409E (collectively referred to as "electrical conductors 409") within electrical connector 403 to permit individual control and activation of each of the electrode array elements 407. Alternatively, various combinations of the electrical array elements 407 may be grouped together. Although electrical conductors 409 are shown in FIG. 5 as accessing respective electrode array elements 407 laterally from a side of electrode array 400, electrical connector 403 may be oriented in any manner to access the electrode array elements, subject to physical constraints presented by a particular external or internal application.

While the electrode array elements 407 are illustrated as a linear series of rectangular elements in this particular embodiment, each of the electrode array elements 407 may be fabricated into any shape and orientation to permit creation of a spatially varying electric field when one or more of the electrode array elements 407 are energized with a different voltage. For example, electrode array elements 407 may be configured in a linear array, a two-dimensional array, or even a three-dimensional array. In this manner, selected electrode array elements 407 can be individually activated to deliver electric fields at different positions and in different directions or planes.

Coating layer 402 surrounds backing layer 401 and each of the electrode array elements 407 to provide a physical barrier between each of the electrode array elements 407 and the external environment. Coating layer 402 also provides an increased overpotential value for each of the electrode array elements 407 when used in biological fluids. Alternatively, coating layer 402 may be selectively applied to cover or protect only the individual electrode array elements 407 formed on backing layer 401. Hence, coating layer 402 may encapsulate array elements 407 and backing layer 401, encapsulate only the array elements, or even encapsulate individual array elements with separate coating layers. Electrode array elements 407 may be formed on backing layer 401 in a variety of ways. For example, electrode array elements 407 may be punched or formed from sheets of conductive material and placed above backing layer 401, e.g., with an adhesive. Alternatively, electrode array elements 407 may be printed or deposited on backing layer 401 using any of a variety conventional deposition processes. Backing layer 401 may be made from a variety of materials, including silicon, ceramic, paper, or polymeric materials.

Figure 6:
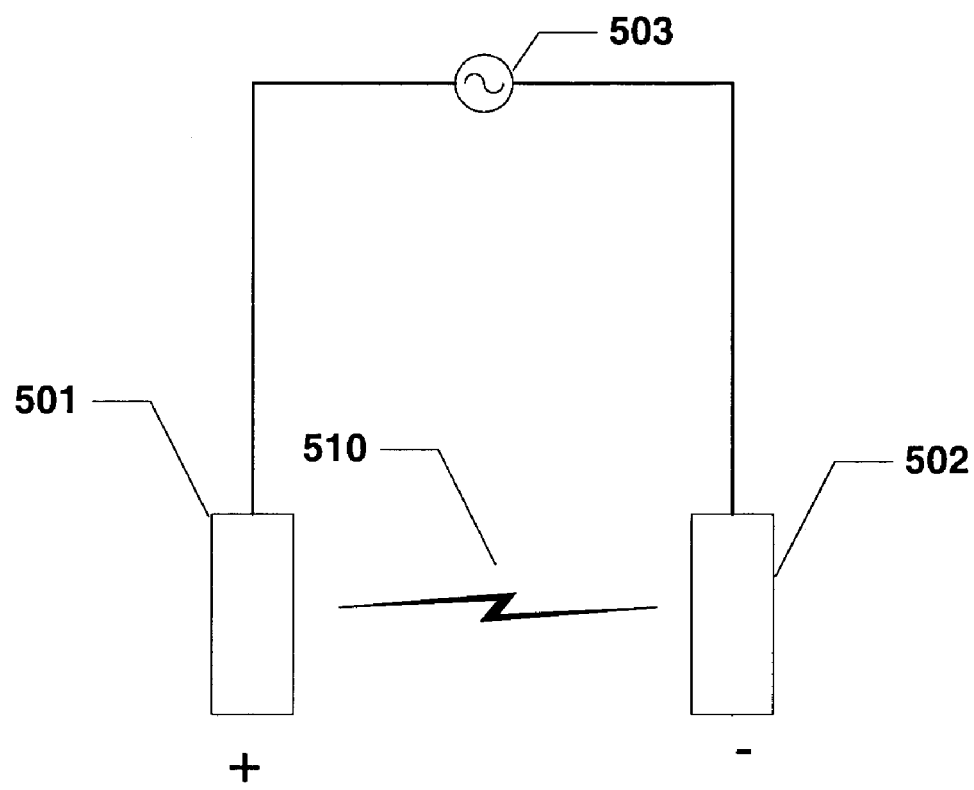
FIG. 6 is a schematic diagram of an externally placed electrode pair used to generate a sustained electric field according to an embodiment of the invention.

FIG. 6 is a schematic diagram of an externally placed, coated electrode pair 501, 502 used to generate a sustained electrical field according to principles of the invention. An electric field 510 is created between a positive electrode 501 and a negative electrode 502 by an appropriate control circuit and power source 503. In this embodiment, the electrodes may be applied externally to a patient's skin. In some cases, sustained electric fields from externally placed electrodes may cause undesired electro-chemical reactions within a hydrogel used to interface the electrode to a patient's skin. As previously explained, the coated electrodes 501, 502 having an increased overpotential may reduce or eliminate these reactions and any negative effects that would otherwise result. An externally placed electrode pair or array, as shown in FIG. 6, may take advantage of the ability of the laminar structure of a patient's skin to decrease its impedance at high frequencies, i.e., greater than approximately 200 to 300 Hz. In this case, a high frequency waveform can be used to establish the electric potential across electrodes 501, 502. A chloride rich buffer layer can be used with a silver/silver chloride reversible electrode approach, in combination with a biphasic waveform in order to produce a reversible reaction at the surface of the electrode, and thus avoiding irreversible deleterious effects of chemical reactions.

Figure 7:
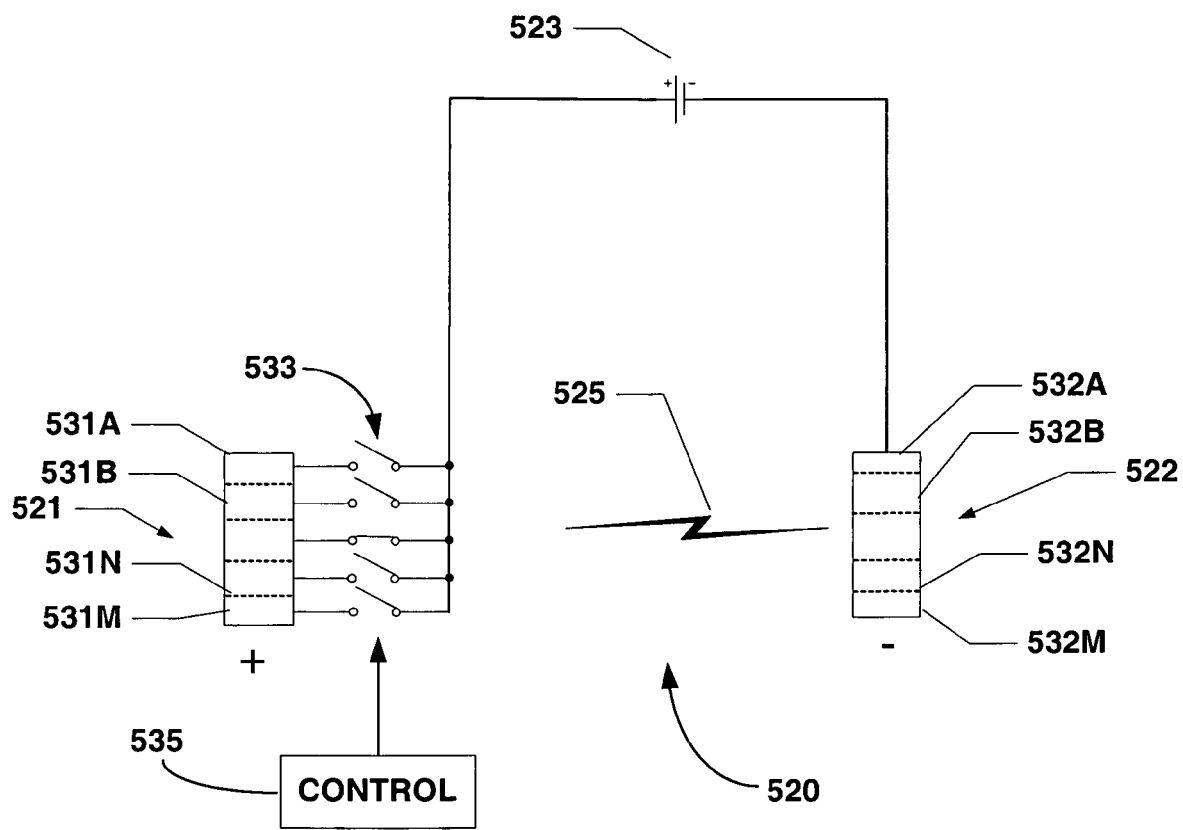
FIG. 7 is a schematic diagram of an externally placed multi-element electrode array used to generate a sustained electric field according to an embodiment of the invention.

FIG. 7 is a schematic diagram of implanted multi-element electrode arrays 521, 522 used to generate an electric field. One or both of electrode arrays 521, 522 may be implanted within the body, or placed subcutaneously. Also, one of electrode arrays 521 may be implanted within the body, with the other array 522 placed subcutaneously or externally. In this particular embodiment, a power source 523 is electrically connected to a pair of electrode arrays 521-522.

A switch array 533 and control circuit 535 selectively create an electric field 525 between the electrode arrays 521, 522. In particular, control circuit 535 opens and closes individual switches in switch array 533 to selectively couple one or more of electrodes 531A-531M to the positive power terminal of power source 523. A similar switch array and control circuit may be provided to selectively couple electrodes 532A-532M of electrode array 522 to the negative terminal of power source 523. Because of the array structure, the electrical field may be varied based upon location. In particular, individual electrodes 531, 532, or groups of electrodes, can be selectively activated according to a desired location or orientation of the electric field, as well as in response to empirical testing that reveals electrode combinations that produce better efficacy, e.g., in terms of therapeutic effect or lack of side effects.

Because electrode arrays 521, 522 include a coating layer that provides a higher overpotential for electrodes 531, 532, adverse reactions are avoided. Whether using arrays or individual electrodes, the application of sustained electric fields can be used to stimulate bone growth, retard bacteria growth, or provide any of a variety of other therapies.

Because of the higher overpotential characteristics of electrode arrays 521, 522, the electrode arrays 521, 522 may be implanted into a patient to allow creation of a sustained electric field 525 at a targeted location while reducing or eliminating adverse electro-chemical reactions that would otherwise cause electrode corrosion and undermine performance. As one example, electrode arrays 521, 522 may be implanted about a heart within a patient's body; however, the electrode arrays 521, 522 may be implanted at any desired location within the body in which electric field therapy is desired. For example, although a target organ may be a human heart, electrodes 521, 522 may be deployed at any implantation site to generate the sustained electric field 525 at a specific location between electrodes 521, 522.

Using electrode arrays 521, 522, a sustained electric field 525 may be initially created using one subset of electrode elements 531, 532 to control the location of the electric field. As therapy progresses, a different subset of electrode elements 531, 532 may be used to alter the electric field generated to a different location or otherwise vary the electrical field. Again, selective activation of electrode elements 531, 532 may be accomplished by a switch array 533 and control circuit 535, as shown in FIG. 7.

Some electrode array elements 531, 532 may be selectively decoupled from power source 523, i.e., turned off, using switch array 533. Alternatively, some electrode array elements 531, 532 may be driven with different voltage or current levels, e.g., with the addition of drive circuitry (not shown) between power source 523 and the electrode array elements. The drive circuitry may be dynamic and responsive to control circuitry 535 to adjust the voltage or current levels applied by power source 523 to selected electrode elements 531, 532. For example, the drive circuitry may include programmable resistor networks or voltage dividers to adjust the voltage or current level delivered to individual electrode elements 531, 532.

As an alternative, each electrode array 521, 522 may be constructed as a "smart" array in which conductor wire resistance or electrode surface impedance (i.e., by material properties or surface area) is tuned to produce a desired output. This latter alternative would generally be a static solution in the sense that the individual electrode elements 531, 532 can be formulated to provide different outputs, but thereafter can not be readily changed without the addition of dynamic drive circuitry as described above. In either case, however, different voltage or current levels can be achieved among the electrode elements 531, 532 to provide an electric field with a desired shape or characteristic.

This feature may be useful or advantageous in areas of varying tissue conductivity, or with tissue or organs of varying shape. As an example, electrode array element 531A may be energized to a particular voltage relative to corresponding electrode array element 532A. Each additional electrode array element 531B-531N may be energized to the same or different voltage values relative to their respective corresponding electrode array element 532B-532N. As such, a subset of the region between electrodes 531, 532 may generate electric field 525.

Additionally, electric field 525 may vary spatially, providing the ability to shape the electric field applied to the patient. For example, if electrode array element pair 531A, 532A possess the highest voltage, if electrode array element pair 531N, 532N possess the lowest voltage, and if electrode element pairs 531B, 532B through 531M, 532M possess a voltage decreasing between the highest and the lowest voltage, electric field 525 will vary correspondingly. All of these variations in potential generated by each electrode array element permit electric field 525 to vary in position without requiring re-implantation.

Electrode arrays 521, 522, having a coating layer in accordance with the present invention, exhibit a higher overpotential relative to exposed electrodes and thus facilitate the generation of higher voltage electric fields. In general, the electrode configurations described herein can improve existing therapies and permit additional therapies by facilitating the creation of higher voltage electrode fields relative to exposed, conventional electrodes, as well as longer sustained fields and/or reduced corrosion.

Figure 8:
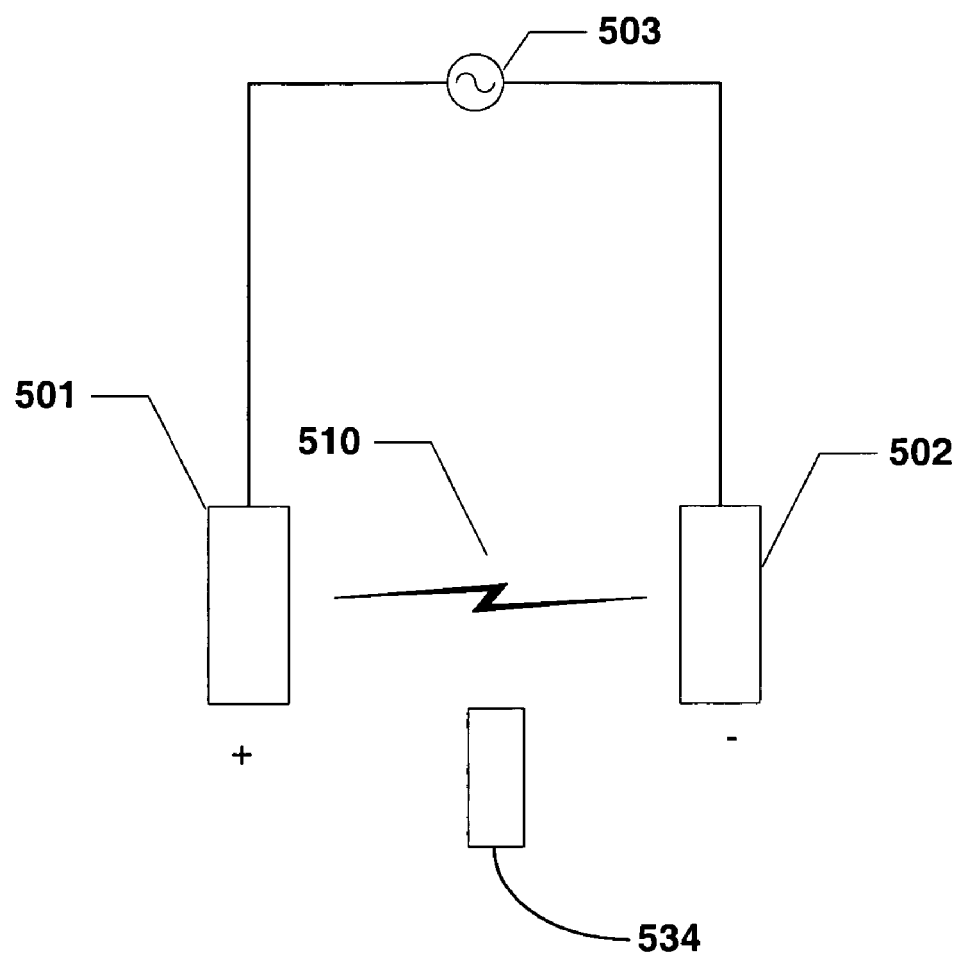
FIG. 8 is a schematic diagram of an internally placed multi-element electrode array used to generate a sustained electric field in conjunction with an implanted component according to an embodiment of the invention.

FIG. 8 is a schematic diagram of implanted multi-element electrodes 501, 502 with an additional implanted component 534. Electric field 510 may be used in combination with implantable component 534 to provide therapies to patients. Implantable component 534 may include, for example, a micro-device, a drug, a protein, or similar material that may be placed within a patient. Implantable component 534 may be implanted at the time electrodes 501, 502 are implanted or may be injected, ingested, inhaled or otherwise delivered into the patient at a later point in time.

In the example of FIG. 8, implantable component 534 is placed near electrodes 501, 502 in proximity to a target location within the patient's body, such as the heart. Electric field 510 interacts with implantable component 534. The electric field 510 is controlled to change or alter properties of implantable component 534, and thereby acts as a catalyst or activating agent for delivery of therapy by the implantable component. For example, the electric field could activate the component 534, could cause it to deliver a drug, could alter or affect a drug, could target specific areas for therapy by the component 534, could move or direct the component 534, or interact in any number of ways.

For example, implantable component 534 may be a microfabricated MEMS device. Such a device may include a mechanical component, such as a valve, that is activated by electric field 510. For example, the valve may be electromagnetically actuated by electric field 510. Alternatively, electric field 510 may serve to power an inductive power supply that generates power in response to energy induced in a coil by the electric field. The induced power may be used to actuate the MEMS device.

Additionally, implantable component 534 may include an electro-active compound, such a drug or protein. In this case, electric field 510 provides energy to trigger the electro-active compound to activate the reaction, thus providing therapy. Alternatively, electro-active compounds may cause a drug in liquid form to flow from implanted component 541 to a region of highest electric field voltage between electrodes 501, 502. As an alternative to individual electrodes 501, 502, electrode arrays may be used. Using an electro-active compound with electrode arrays, e.g., as shown in FIG. 7, the compound may be selectively activated or concentrated at different locations. For example, voltages may be altered on each of the electrode array elements to cause the compound to concentrate at various locations between the electrodes, providing targeted application of the drug to a desired region with greater precision.

Applications for this improved electrode may include the localized delivery of a drug into tissue that is activated by the sustained electric field 525. In addition, the ability to sustain the use of improved electrodes 501, 502 within a patient using intelligent electrodes consisting of multiple individually activated electrode elements within a larger electrode structure provides additional levels of control and delivery.

Figure 9:
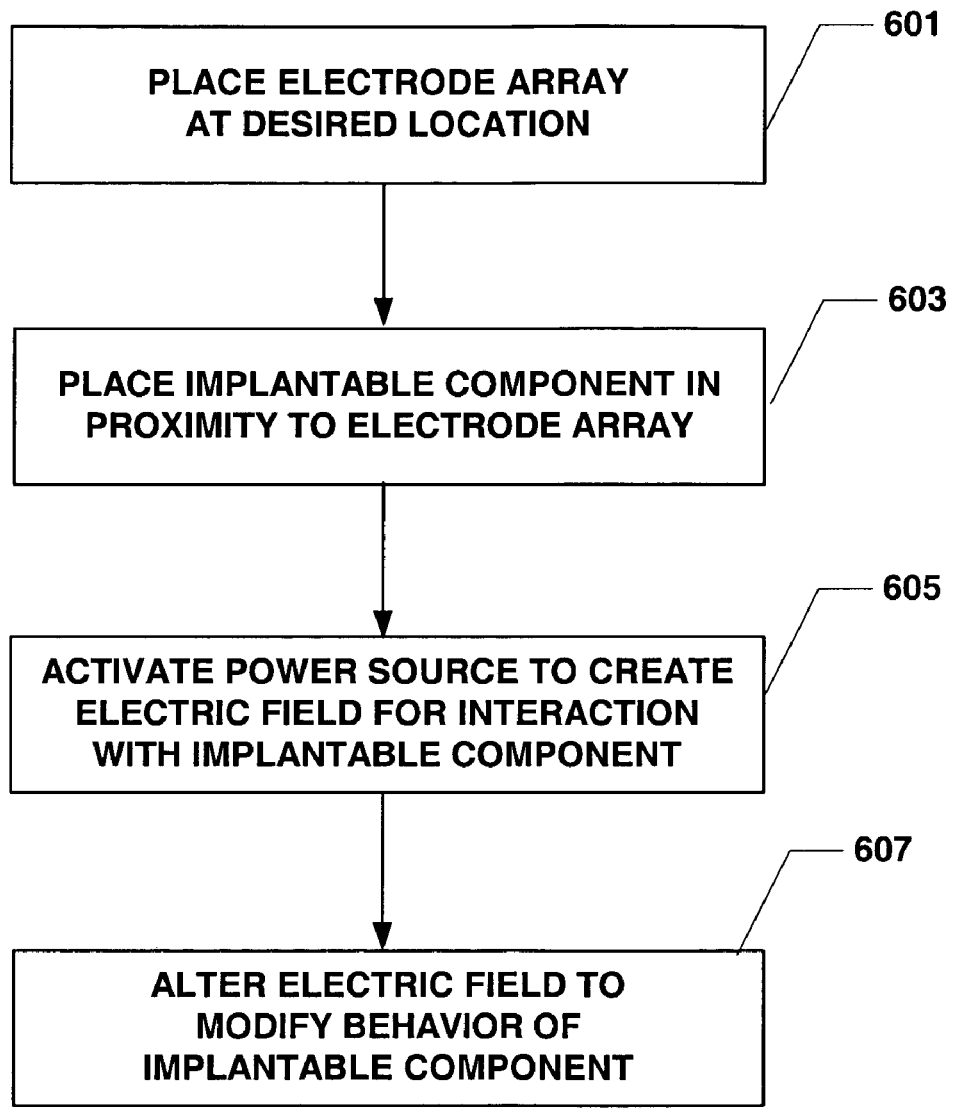
FIG. 9 is a flowchart illustrating an exemplary method for creating a sustained electric field in conjunction with an implanted component according to an embodiment of the invention.

FIG. 9 is a flowchart illustrating an example method for creating an electrical field according to an embodiment of the present invention. The electrode structure, such as an electrode array, is placed (601) at a desired location on or implanted within a patient. Optionally, an additional implantable component is ingested, injected, implanted, or otherwise delivered to a patient site (603) in proximity to the electrodes. Upon activating a power source to create an electric field, the implantable component interacts with the electric field between the electrodes to provide therapy to a patient (605). The electric field can be altered to modify the behavior of the implantable component (607), e.g., to chemically or electromagnetically release a therapeutic substance, or to actuate a micro-device such as a valve to release such a substance. Alternatively, the electric field itself (i.e., with no additional implantable component) may be used to provide therapy.

The electric field may be either ac or dc. In addition, both mono-phasic pulsed fields and bi-phasic pulsed fields may be generated. With a coating layer as described herein, an appropriately configured electrode pair may be capable of supporting an electric potential of greater magnitudes, including magnitudes of greater than or equal to approximately one volt, on a sustained basis of greater than or equal to approximately one second. In some embodiments, the potential applied to the electrode may be in a range of approximately 1 to 1000 volts, and more preferably approximately 10 to 50 volts, although the appropriate potential will vary according to the size of the electrode, the distance between electrodes, the material used to construct the electrodes, the thickness of the coating layer, and other physical characteristics that influence the magnitude of the electric field generated by the electrodes in response to the applied potential. In some embodiments, the potential may be applied on a sustained basis, either as a continuous or alternating potential, for several seconds, minutes, hours, or even days. In each case, the electrode can support an increased electric field on a sustained basis to provide a prolonged course of therapy.

Figure 10:
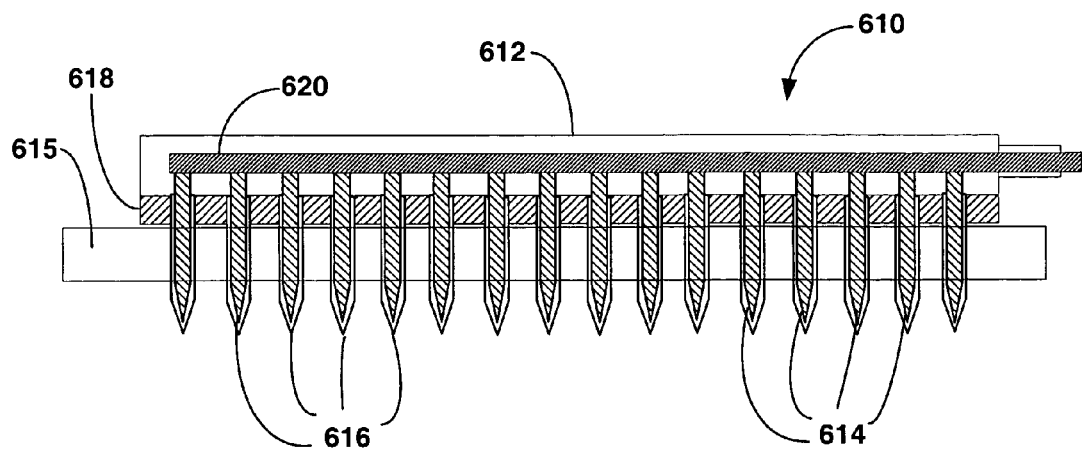
FIG. 10 is a side view of a percutaneous electrode array according to an embodiment of the invention.
Figure 11:
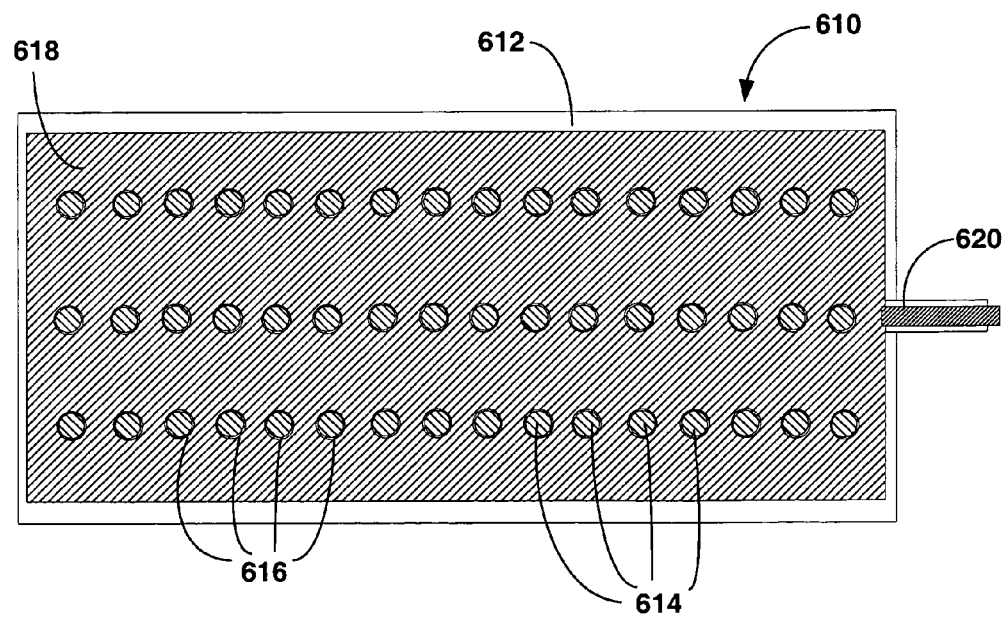
FIG. 11 is a plan view of a bottom side of the percutaneous electrode array of FIG. 10.

As described herein, the principles of the invention may be applied to implanted electrodes, including subcutaneously implanted electrodes, as well as external electrodes. FIG. 10 is a side view of a percutaneous electrode array 600 in accordance with another embodiment of the invention. FIG. 11 is a bottom plan view of percutaneous electrode array 610. In the example of FIGS. 10 and 11, percutaneous electrode array 610 includes a base plate 612 having a plurality of needle-like electrode extensions 614. Each electrode extension 614 is made from an electrically conductive material, and has a sharpened tip designed to perforate and penetrate a layer of skin 615 on a patient upon application of pressure.

Base plate 612 may be made from an electrically conductive material, and be coupled across electrode extensions 614 to simultaneously deliver electrical energy to all of the electrode extensions. Alternatively, base plate 612 may be constructed from a dielectric material, in which case electrode array 610 may include one or more electrical conductors, represented by conductor 620, which deliver energy to electrode extensions 614 either in common or individually. Further, in accordance with the invention, each needle-like electrode extension 614 includes a coating layer 616, which is constructed from materials as described herein. In particular, the coating layer 616 provides a barrier between each electrode extension 614 and the environment in which the electrode extension is used, and increases the overpotential of the electrode extension to eliminate or reduce corrosion due to electro-chemical reactions. In this manner, electrode array 610 is capable of delivering higher voltages to support high electric fields on a sustained basis for delivery of therapy to a patient.

In some embodiments, electrode array 610 further includes a localized, anti-biotic release layer 618 to prevent infection upon penetration of skin layer 615 with needle-like electrode extensions 614. Electrode extensions 614 may be arranged in a linear array. Alternatively, as shown in the plan view of FIG. 11, a two-dimensional array of electrode extensions 614 may protrude from base plate 612, e.g., as a series of rows or columns. In either case, electrode extensions 614, in combination with coating layers 616 is capable of generating a uniformly distributed electric field on a sustained basis for a prolonged period of time, aiding in subcutaneous therapy.

While various embodiments of the invention have been described, additional modifications and embodiments may be made without departing from the scope of the claims. These and other embodiments are within the scope of the following claims.

The invention claimed is:

1. An electrode comprising:
   an electrically conductive, monolithic substrate layer;
   an elongated electrical conductor having an insulating cover layer and coupled to the conductive substrate layer; and
   an electrically non-insulating, coating layer covering the substrate layer, wherein the coating layer provides an increased overpotential for the electrode in a fluid.

2. The electrode according to claim 1, wherein the overpotential is increased relative to an equilibrium potential of a reference electrode.

3. The electrode according to claim 2, wherein the reference electrode is a saturated calomel electrode and the overpotential increase is at least approximately 1.2 volts.

4. The electrode according to claim 2, wherein the reference electrode is a saturated calomel electrode and the overpotential increase is at least approximately 1.8 volts.

5. The electrode according to claim 1, wherein the coating layer comprises a boron-doped diamond material having boron ions in a concentration of between 2,000 to 10,000 parts per million.

6. The electrode according to claim 1, wherein the coating layer includes a dopant and a material selected from the group consisting of: diamond, diamond-like carbon, borosilicate glass, carbides, nitrides.

7. The electrode according to claim 1, wherein the coating layer includes a doped dielectric material.

8. The electrode according to claim 1, wherein the coating layer has a thickness between approximately 2 and 10 nm.

9. The electrode according to claim 1, wherein the coating layer has a thickness between approximately 1 and 100 nm.

10. The electrode according to claim 1, wherein the substrate layer comprises a plurality of electrode array elements.

11. The electrode according to claim 10, wherein the electrical conductor includes a plurality of electrical conductors, and each of the electrode array elements is separately coupled to a separate one of the electrical conductors.

12. The electrode according to claim 10, wherein each of the electrode array elements is individually actuable to generate an electric field independently of the other electrode array elements.

13. The electrode according to claim 1, wherein the electrically conductive substrate includes a metal.

14. The electrode according to claim 1, wherein the coating layer is sputtered or vapor deposited.

15. The device according to claim 14, further comprising an implantable component configured to deliver a therapy upon interaction with the electric field.

16. The device according to claim 1, wherein the implantable component includes a device that releases a therapeutic substance upon interaction with the electric field.

17. The device according to claim 16, wherein the therapeutic substance includes an injected, ingested, or inhaled substance.

18. A medical device comprising:
a first electrode having a first electrically conductive, monolithic substrate layer, a first elongated electrical conductor having an insulating cover layer and coupled to the first substrate layer, and a first non-insulating, coating layer covering the first substrate layer, wherein the first coating layer provides an increased overpotential for the first electrode in a fluid;
a second electrode having a second electrically conductive, monolithic substrate layer, a second elongated electrical conductor having an insulating cover layer and coupled to the conductive substrate layer, and a second electrically non-insulating coating layer covering the second substrate layer, wherein the second coating layer provides an increased overpotential for the second electrode in a fluid;
an electrical power source coupled to apply a substantially continuous electric potential across the first and second elongated electrical conductors.

19. The medical device of claim 18, wherein the electrical power source applies a substantially continuous electric potential of greater than or equal to approximately one volt across the first and second electrical conductors for a period of greater than or equal to approximately one second.

20. The device according to claim 18, wherein the overpotential is increased relative to an equilibrium potential of a reference electrode.

21. The device according to claim 18, wherein the reference electrode is a saturated calomel electrode and the overpotential increase is at least approximately 1.2 volts.

22. The device according to claim 18, wherein the reference electrode is a saturated calomel electrode and the overpotential increase is at least approximately 1.8 volts.

23. The device according to claim 18, wherein each of the first and second coating layers comprises a boron-doped diamond material having boron ions in a concentration of at between about 2,000 to 10,000 parts per million.

24. The device according to claim 18, wherein each of the first and second coating layers includes a dopant and a material selected from the group consisting of: diamond, diamond-like carbon, borosilicate glass, carbides, nitrides.

25. The device according to claim 18, wherein each of the first and second coating layers includes a doped dielectric material that increases the overpotential by at least approximately 1.2 volts.

26. The device according to claim 18, wherein each of the first and second coating layers includes a doped dielectric material.

27. The device according to claim 18, wherein each of the first and second coating layers has a thickness between approximately 2 and 10 nm.

28. The device according to claim 18, wherein each of the first and second coating layers has a thickness between approximately 1 and 100 nm.

29. The device according to claim 18, wherein each of the first and second substrate layers comprises a plurality of electrode array elements.

30. The device according to claim 29, wherein each of the electrical conductors includes a plurality of electrical conductors, and each of the electrode array elements is separately coupled to a separate one of the electrical conductors.

31. The device according to claim 29, wherein each of the electrode array elements is individually actuable to generate an electric field independently of the other electrode array elements.

32. The device according to claim 18, wherein each of the first and second electrically conductive substrates includes a metal.

33. The device according to claim 18, wherein each of the first and second coating layers is sputtered or vapor deposited.

34. The device according to claim 18, wherein the electric potential is a time varying electric potential.

35. The device according to claim 18, wherein the electric potential is a non-time varying electric potential.

36. An electrode comprising:
an electrically conductive, monolithic substrate layer;
an elongated electrical conductor having an insulating cover layer and coupled to the conductive substrate layer; and
an electrically non-insulating, coating layer formed of a material comprising a boron dopant covering the substrate layer, wherein the coating layer provides an increased overpotential for the electrode in a fluid without substantially increasing an impedance of the electrode as compared to a coating layer formed of the material without a dopant.

37. An electrode comprising:
an electrically conductive, monolithic substrate layer;
an elongated electrical conductor having an insulating cover layer and coupled to the conductive substrate layer; and
an electrically non-insulating, coating layer formed of a material comprising a boron dopant covering the substrate layer, wherein the coating layer provides an increased overpotential for the electrode in a fluid.

* * * * *